(12) United States Patent
Wilkinson et al.

(10) Patent No.: US 9,339,396 B2
(45) Date of Patent: May 17, 2016

(54) ROBOTIC EXOSKELETON MULTI-MODAL CONTROL SYSTEM

(71) Applicant: HARRIS CORPORATION, Melbourne, FL (US)

(72) Inventors: Loran J. Wilkinson, Palm Bay, FL (US); Paul M. Bosscher, West Melbourne, FL (US); Matthew D. Summer, Melbourne, FL (US)

(73) Assignee: Harris Corporation, Melbourne, FL (US)

( * ) Notice: Subject to any disclaimer, the term of this patent is extended or adjusted under 35 U.S.C. 154(b) by 0 days.

(21) Appl. No.: 14/452,851

(22) Filed: Aug. 6, 2014

(65) Prior Publication Data

US 2015/0289995 A1 Oct. 15, 2015

Related U.S. Application Data (60) Provisional application No. 61/978,545, filed on Apr. 11, 2014.

(51) Int. Cl.
*G05B 19/04* (2006.01)
*A61F 2/60* (2006.01)
*B25J 19/00* (2006.01)
*B25J 9/00* (2006.01)
*A61F 2/68* (2006.01)
*A61F 2/70* (2006.01)
(Continued)

(52) U.S. Cl.
CPC ... *A61F 2/60* (2013.01); *A61F 2/68* (2013.01); *A61F 2/70* (2013.01); *B25J 9/0006* (2013.01); *B25J 19/0091* (2013.01); *A61F 2002/5081* (2013.01); *A61F 2002/701* (2013.01); *A61F 2002/741* (2013.01); *A61F 2002/745* (2013.01); *Y10S 901/49* (2013.01)

(58) Field of Classification Search
USPC .............. 700/245, 258, 261, 246, 250; 602/6; 600/587, 592, 595; 901/27, 28, 46; 318/1, 8, 9, 17
See application file for complete search history.

(56) References Cited

U.S. PATENT DOCUMENTS

| | | |
|---|---|---|
| 5,516,249 A | 5/1996 | Brimhall |
| 5,583,478 A | 12/1996 | Renzi |
| 7,190,141 B1 | 3/2007 | Ashrafiuon et al. |

(Continued)

OTHER PUBLICATIONS

Rahman, T., et al., "Passive Exoskeletons for Assisting Limb Movement," Journal of Rehabilitation Research & Development, vol. 43, No. 5, pp. 583-590, Aug./Sep. 2006, DOI: 10.1682/JRRD.2005.04.0070.

(Continued)

*Primary Examiner* — Ronnie Mancho
(74) *Attorney, Agent, or Firm* — Fox Rothschild LLP; Robert J. Sacco; Carol E. Thorstad-Forsyth (57) ABSTRACT

System and method for operating a robotic exoskeleton involves using a control system (107) to monitor an output one or more electrical activity sensors (202) disposed on a human operator. The control system determines if an output of the electrical activity sensors corresponds to a predetermined neural or neuromuscular condition of the user. Based on the determining step, the control system automatically chooses an operating mode from among a plurality of different operating modes. The operating mode selected determines the response the control system will have to control inputs from the human operator.

14 Claims, 4 Drawing Sheets

(51) Int. Cl.
  *A61F 2/50* (2006.01)
  *A61F 2/74* (2006.01)

(56) References Cited

U.S. PATENT DOCUMENTS

| | | | |
|---|---|---|---|
| 7,300,824 | B2 | 11/2007 | Sheats |
| 7,665,641 | B2 * | 2/2010 | Kaufman ............... A45F 3/14 224/261 |
| 7,774,177 | B2 | 8/2010 | Dariush |
| 7,947,004 | B2 | 5/2011 | Kazerooni et al. |
| 8,142,370 | B2 | 3/2012 | Weinberg et al. |
| 8,419,804 | B2 | 4/2013 | Herr et al. |
| 8,702,811 | B2 | 4/2014 | Ragnarsdottir et al. |
| 8,849,457 | B2 | 9/2014 | Jacobsen et al. |
| 8,986,397 | B2 | 3/2015 | Bedard et al. |
| 9,066,817 | B2 | 6/2015 | Gilbert et al. |
| 2006/0079817 | A1 | 4/2006 | Dewald et al. |
| 2007/0123997 | A1 | 5/2007 | Herr et al. |
| 2008/0009771 | A1 * | 1/2008 | Perry .................... B25J 9/0006 600/587 |
| 2008/0249438 | A1 | 10/2008 | Agrawal et al. |
| 2009/0255531 | A1 | 10/2009 | Johnson et al. |
| 2010/0113980 | A1 * | 5/2010 | Herr ...................... A61F 2/60 600/587 |
| 2010/0114329 | A1 | 5/2010 | Casler et al. |
| 2011/0040216 | A1 | 2/2011 | Herr et al. |
| 2011/0266323 | A1 | 11/2011 | Kazerooni et al. |
| 2012/0156661 | A1 | 6/2012 | Smith et al. |
| 2012/0259431 | A1 | 10/2012 | Han et al. |
| 2013/0102935 | A1 | 4/2013 | Kazerooni et al. |
| 2013/0296746 | A1 | 11/2013 | Herr et al. |
| 2013/0310979 | A1 * | 11/2013 | Herr ...................... B25J 9/1694 700/258 |
| 2014/0094728 | A1 * | 4/2014 | Soderberg ............. A61F 5/028 602/6 |
| 2015/0088043 | A1 * | 3/2015 | Goldfield ............... A61F 5/01 602/6 |
| 2015/0289995 | A1 * | 10/2015 | Wilkinson ........... B25J 19/0091 623/27 |

OTHER PUBLICATIONS

Rosen, J., et al., "A Myosignal-Based Powered Exoskeleton System," IEE Transaction on Systems, Man, and Cybernetics—Part A: Systems and Humans, vol. 31, No. 3, May 2001, 1083-4427/01, copyright 2001 IEEE.

Burkard, H., et al., "An Ultra-Thin, Highly Flexible Multilayer," http://www.hightec.ch/uploads.media/An_ultra_thin_highly_flexible_multilayer_2007_01.pdf.

Banala, S.K., et al., "Gravity-Balancing Leg Orthosis and Its Performance Evaluation," IEEE Transactions on Robotics, vol. 22, No. 6, Dec. 2006, 1552-3098, copyright 20006 IEEE.

Goswami, A., "Active Empedance: A Noval Concept in Assistive Exoskeleton Control," Exoskeleton Control Using Active Impedance, This work is a collaboration with Prof. Ed Colgate, Prof. Michael Peshkin and Gbriel-Aguirre Ollinger of Northwestern University, Evanston, Illinois, page last updated Sep. 24, 2012.

Huang, J., et al., "Human Motion Assistance Using Waling-Aid Robot and Wearable Sensors," In Proceedings of the International Congress on Neurotechnology, Electronics and Informatics (RoboAssist-2013), pp. 199-204, ISBN: 78-989-8565-80-8, DOI: 10.5220/0004664101990204, copyright 2013 SCITEPRESS (Science and Technology Publications, Lda.).

Wolbrecht, E.T., et al., "Pneumatic Control of Robots for Rehabilitation," The International Journal of Robotics Research, vol. 29, No. 1, Jan. 2010, pp. 23-38, DOI: 10.1177/0278364909103787, copyright The Author(s), 2010.

Debicki, D.B., et al., "Inter-Joint Coupling Strategy During Adaptation to Novel Viscous Loads in Human Arm Movement," J. Neurophysiol 92: 754-765, 2004; 10.1152/jn.00119.2004, 022-3077/04, copyright 2004 The American Physiological Society.

Jung, J., et al., "Walking Intent Detection Algorithy for Paraplegic Patients Using a Robotic Exoskeleton Waling Assistant with Crutches," International Journal of Control, Automatiion, and Systems (2012) 10(5):954-962 DOI: 10.1007/s12555-01200512-4, ISSN:1598-6446 eISSN:2005-4092; copyright ICROS, KIEE and Springer 2012.

Lenzi, T., et al., "Intention-Based EMG Control for Powered Exoskeletons," IEEE Transactions of Biomedical Engineering, vol. 59, No. 8, Aug. 2012, 0018-9294 copyright 2012 IEEE.

Dorrier, Jason, "New Upper Body Bionic Suit Uses Air to Lift Loads of 50 Kilograms," Oct. 16, 2012, Augmentation, Video Post, http://singularityhub.com/2012/10/16/new-upper-body-bionic-suit-uses-air-to-lift-loads-of-50-kilograms/.

Black, Thomas, Business Bet on Iron Man-Like Exoskeletons, Businessweek, Mar. 28, 2013 http://www.bloomberg.com/bw/articles/2013-03-28/businesses-bet-on-iron-man-like-exoskeletons.

Upbin, Bruce, "This Amazing Robot Exoskeleton Helps the Paralyzed Walk Again," Nov. 8, 2013, Forbes.

Bowdler, Neil, "Rise of the Human Exoskeletons," Technology, BBC News, Mar. 4, 2014.

Robotics Laboratory, "Static and Dynamic Balancing of Parallel Mechanisms," University Laval, copyright 1997-2015 Laboratoire de robotique.

Robotics (http://news.discovery.com/tech/robotics), "I am Iron Man: Top 5 Exoskeleton Robots," Nov. 27, 2012, Associated Press,U.S. Army.

Huang, J., et al., "Human Motion Assistance Using Walking-Aid Robot and Wearable Sensors," Abstract Only, RoboAssist 2013—Special Session on Wearable Robotics for Motion Assistance and Rehabilitation Abstracts, http://neurotechnix/org/Abstracts/2013/RoboAssist)2013_Abstracts/htm.

* cited by examiner

ROBOTIC EXOSKELETON MULTI-MODAL CONTROL SYSTEM

CROSS REFERENCE TO RELATED APPLICATIONS

This application claims the benefit of U.S. Provisional Patent Application No. 61/978,545, filed Apr. 11, 2014, the entirety which is incorporated herein by reference.

BACKGROUND OF THE INVENTION

1. Statement of Technical Field

The inventive arrangements relate to robotic exoskeletons and more particularly to robotic exoskeletons having advanced control systems that facilitate improved operation.

2. Description of the Related Art

A robotic exoskeleton is a machine that is worn by a human user. Such machines typically comprise a structural frame formed of a plurality of rigid structural members. The structural members are usually connected to each other at a plurality of locations where joints or articulated members allow movement of the structural members in a manner that corresponds to movement in accordance with the human anatomy. When the exoskeleton is worn by a user, the location of many of the robotic joints will often correspond to the location of joints in the human anatomy. Motive elements, which are sometimes called actuators, are commonly used to facilitate movement of the rigid structural members that comprise the exoskeleton. These motive elements or actuators commonly include hydraulic actuators, pneumatic actuators and/or electric motors. Various exoskeleton designs for humans have been proposed for the full body, lower body only, and upper body only.

An exoskeleton includes a power source to operate the motive elements or actuators. The power source for such devices can be an on-board system (e.g. batteries, or fuel driven power generator carried on the exoskeleton). Alternatively, some exoskeleton designs have a wire or cable tether which supplies power (e.g. electric or hydraulic power) from a source which is otherwise physically independent of the exoskeleton. An on-board control system is provided in many exoskeletons to allow a user to control certain operations of the exoskeleton. Due to the close interaction of the exoskeleton with the human operator, such a control system for the exoskeleton must be carefully designed to facilitate ease of use and operator safety.

Robotic exoskeletons as described herein can provide users with advantages of increased strength, endurance and mobility. The motive elements used to produce movement of the structural members forming the exoskeleton can in many designs exert forces that far exceed the strength and/or endurance of a human. Exoskeletons can also potentially increase user safety and help control certain desired motions. As such, robotic exoskeletons are of increasing interest for use in a wide variety of applications. For example, robotic exoskeletons have potential for use in the fields of healthcare, physical rehabilitation, and public service (police, first responders). Exoskeletons also show promise for use in areas such as human augmentation.

SUMMARY OF THE INVENTION

The inventive arrangements concern a robotic exoskeleton. A robotic exoskeleton is comprised of a plurality of structural members, one or more robotic joints at which the plurality of structural members are movably attached, and a plurality of actuators connected to the structural members which are capable of providing a motive force for moving the structural members in relation to the robotic joints. The structural members and robotic joints of the exoskeleton are arranged to facilitate movement of the exoskeleton in conformance with at least a portion of a human anatomy when the exoskeleton is worn by a user. A controller generates actuator control signals that control the actuators in response to a plurality of input signals to produce a movement of the exoskeleton. The controller is responsive to one or more sensor inputs which allow the controller to at least partially conform the movements of the exoskeleton to the movements of the operator. At least some of the sensors inputs are provided by neural or neuromuscular sensors. For example, such sensors can include one or more electrical activity sensors, which are arranged to directly sense neural or neuromuscular electrical signals associated with a body of an exoskeleton user. Exemplary neuromuscular sensors include myoelectric sensors. Myoelectric sensors are used to detect electrical potentials generated by muscle cells when these cells are neurologically activated. Myoelectric sensors are usually disposed on the skin on or adjacent to a skeletal muscle of interest. Exemplary neural sensors include EEG sensors. As is known in the art, EEG sensors are usually disposed along the scalp of a person to measure voltage fluctuations resulting from current flow within the neurons of the brain. Neural sensors could also be located at other locations to sensing neural signals. Other types of sensors can also be used which are capable of directly sensing neural or neuromuscular activity. For purposes of the present disclosure, these types of sensors are said to directly measure such activity to differentiate them from other types of sensors (e.g. motion sensors) which measure the secondary effects of such neural or neuromuscular activity (i.e, physical motion) rather than the actual neural or neuromuscular activity which is usually electrical in nature.

According to one aspect of the invention, the controller is responsive to a predetermined output from the one or more electrical activity sensors to select a controller operating mode. The controller operating mode is selected from among a plurality of different operating modes. The operating mode determines the response the control system will have to control inputs from the human operator. As such, the same user input can result in a different exoskeleton action when the controller is set to different operating modes.

The invention also concerns a method for operating a robotic exoskeleton worn by a human operator. The method involves using a control system to monitor an output of one or more electrical activity sensors disposed on the human operator when the human operator is wearing the exoskeleton. The electrical activity sensors allow the control system to directly sense electrical signals associated with the human operator. These electrical signals can include electrical potentials generated by muscle cells when these cells are neurologically activated and/or voltage fluctuations resulting from current flow within the neurons of the brain. The method further involves determining if an output of the electrical activity sensors corresponds to a predetermined output pattern stored in a computer memory of the exoskeleton. Based on the determining step, the control system automatically chooses an operating mode from among a plurality of different operating modes. The operating mode selected determines the response the control system will have to control inputs from the human operator.

BRIEF DESCRIPTION OF THE DRAWINGS

Embodiments will be described with reference to the following drawing figures, in which like numerals represent like items throughout the figures, and in which.

DETAILED DESCRIPTION

The invention is described with reference to the attached figures. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operation are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

A robotic exoskeleton is comprised of a plurality of structural members, one or more robotic joints at which the plurality of structural members are movably attached, and a plurality of actuators connected to the structural members which are capable of providing a motive force for moving the structural members in relation to the robotic joints. The structural members and robotic joints of the exoskeleton are arranged to facilitate movement of the exoskeleton in conformance with at least a portion of a human anatomy when the exoskeleton is worn by a user. A controller generates actuator control signals that control the actuators in response to a plurality of input signals to produce a movement of the exoskeleton.

Due to the close interaction of the exoskeleton with the human operator, a control system for the exoskeleton must be carefully designed to facilitate optimal operator comfort, control and safety. But exoskeletons are often required to perform widely varying types of activities under diverse operating scenarios. For example, certain activities which can be described as "controlled activities" will generally involve relatively low-force levels and/or low-velocity actions. Examples of such activities include the handling of small (sometimes delicate) objects, and moving around within a dwelling. In this scenario, it is desirable for the exoskeleton to function in a way that is substantially "transparent" to the user. The movement of the exoskeleton in these scenarios should closely match the movement of the user and should not require noticeable effort by the operator to control. Also, the exoskeleton should not exert noticeable amounts of force on the user. Ideally, the actuators of the exoskeleton should exert enough force to hold up the weight of the exoskeleton, but should not exert additional force on objects (e.g. small objects) beyond that which is applied by the operator. The goal in this scenario is for the user to be able to feel and receive tactile feedback from his environment, while simultaneously having precise control over the forces exerted by the exoskeleton.

In contrast to the above-described "controlled activities", there will also be times during which it is desirable for the exoskeleton to function in a way that involves enhanced levels of force. As used herein, enhanced levels of force refer to forces that exceed or greatly exceed those forces which the operator is otherwise capable of providing. Sometimes, these high force activities may also need to be performed at high velocity. For convenience, these types of high-force/high velocity actions are referred to herein as "explosive activities." Explosive activities as described herein will generally involve a lesser degree of precision with regard to operator control and a lesser expectation of tactile feedback. Of course, there can also be one or more intermediate levels of activity that require control functions intermediate of the controlled and explosive modes described herein.

There are substantial differences as between exoskeletons (and their associated control systems) which are designed to perform explosive activities versus the controlled activities described above. Accordingly, exoskeletons and especially the control systems for such exoskeletons have been conventionally designed to operate exclusively in one mode (controlled activity mode) or the other (explosive activity mode). As will be appreciated, it is inconvenient and awkward for an operator to use a different exoskeleton or manually reconfigure an exoskeleton as the operator transitions between operations involving two or more different operating modes. Accordingly, the inventive arrangements described herein involve exoskeletons and exoskeleton control systems which are capable of automatically transitioning between the above-described controlled activities and explosive activities in a way that is both automatic and substantially transparent to the operator.

According to one aspect of the present invention, a controller used to control the operation of the exoskeleton is responsive to one or more sensor inputs which allow the controller to at least partially conform the movements of the exoskeleton to the movements of the operator. At least some of the sensors inputs are provided by one or more electrical activity sensors, which are arranged to sense electrical signals associated with an exoskeleton user. Exemplary electrical signals which can be sensed for this purpose include electrical potentials generated by muscle cells when these cells are neurologically activated (neuromuscular electrical signals) and/or voltage fluctuations resulting from current flow within the neurons of the brain (neural electrical signals). When the inputs received by the controller indicate the occurrence of a particular neural or neuromuscular condition, such occurrence can be used to select a controller operating mode. For example, the controller can be responsive to a predetermined output or signal pattern received from the one or more electrical activity sensors to select a controller operating mode. With the foregoing arrangement, the controller operating mode is automatically selected from among a plurality of different operating modes. The operating mode determines the response the control system will have to control inputs from the human operator. As such, the same user input can result in a different exoskeleton action when the controller is set to different operating modes.

The predetermined outputs are identified by evaluating outputs of the neural or neuromuscular sensors to detect a particular nervous system or muscular condition. As an example, the control system can analyze the output of electrical activity sensors to determine if they correspond to or correlate with certain electrical signal patterns which are stored in a memory location accessible to the controller. These stored electrical signal sensor patterns are compared in real time to the actual electrical system sensor outputs. When a sufficient correlation exists between a stored pattern and a measured pattern, the controller will automatically set the controller to a certain operating mode assigned to the stored pattern. The stored electrical system sensor pattern could be a pattern associated with an output of a single sensor. However, it can be advantageous to instead define a stored pattern based on outputs from two or more such sensors. For example, the stored pattern can be based on outputs from an array of electrical system sensors disposed on the operator's body to measure electrical signals from various locations (e.g. multiple skeletal muscles and/or multiple locations on the scalp). Further, it should be appreciated that the electrical activity sensors described herein represent one possible way to sense neural or neuromuscular activity; but the invention is not limited in this regard. Instead, any other technique now known or known in the future can be used to sense such neural or neuromuscular activity.

The plurality of controller operating modes can be chosen to include an explosive activity operating mode and a controlled activity operating mode. In the explosive activity operating mode, the controller exercises control over the actuators in a way that provides amplification of those forces exerted by the user. Conversely, in the controlled activity operating mode, the controller exercises control over the actuators in a way that closely matches the forces exerted by the user.

Additional sensing elements can be provided in the exoskeleton to enhance its performance. For example, the additional sensing elements can include position sensors, force sensors, and acceleration sensors. These sensors can be used sense user motions which are then used by the controller to control the exoskeleton. For example, the controller can utilizes output signals from one or more of the position sensors, force sensors and acceleration sensors to determine a user motion with greater accuracy as compared to that which would be possible when using only the electrical activity sensors. Thereafter, information concerning the user motion is used by the controller to determine a movement of the exoskeleton. Accordingly, the output from the one or more electrical activity sensors can be used to initiate an exoskeleton motion, and then outputs from one or more of the position sensor, the force sensor and the acceleration sensor can be used to more precisely determine the parameters of the motion which has been initiated. Consequently, the control system can utilize electrical activity sensors advantageously in conjunction with these other types of sensors. More particularly, electrical activity sensors can be used by the control system to initiate motion with less delay, and inputs from other sensors can then be used to more precisely control the initiated motion.

The invention also concerns a method for operating a robotic exoskeleton worn by a human operator. The method involves using a control system to monitor an output one or more sensors disposed on the human operator when the human operator is wearing the exoskeleton. The sensors allow the control system to directly sense neural and neuromuscular activity of the human operator. The method further involves determining if an output of the sensors indicates the occurrence of a particular nervous system condition. For example, if electrical activity sensors are used to sense neural and/or neuromuscular activity, then the method can involve evaluating the electrical activity to determine if the particular nervous system condition has occurred. One exemplary approach for making such a determination could involve a determination as to whether a particular pattern of sensed electrical activity corresponds or is otherwise correlated with a predetermined output pattern stored in a computer memory of the exoskeleton. Still, the invention is not limited in this regard and other evaluation methods could also be used. Based on the determining step, the control system automatically chooses an operating mode from among a plurality of different operating modes. The operating mode selected determines the response the control system will have to control inputs from the human operator.

Figure 1:
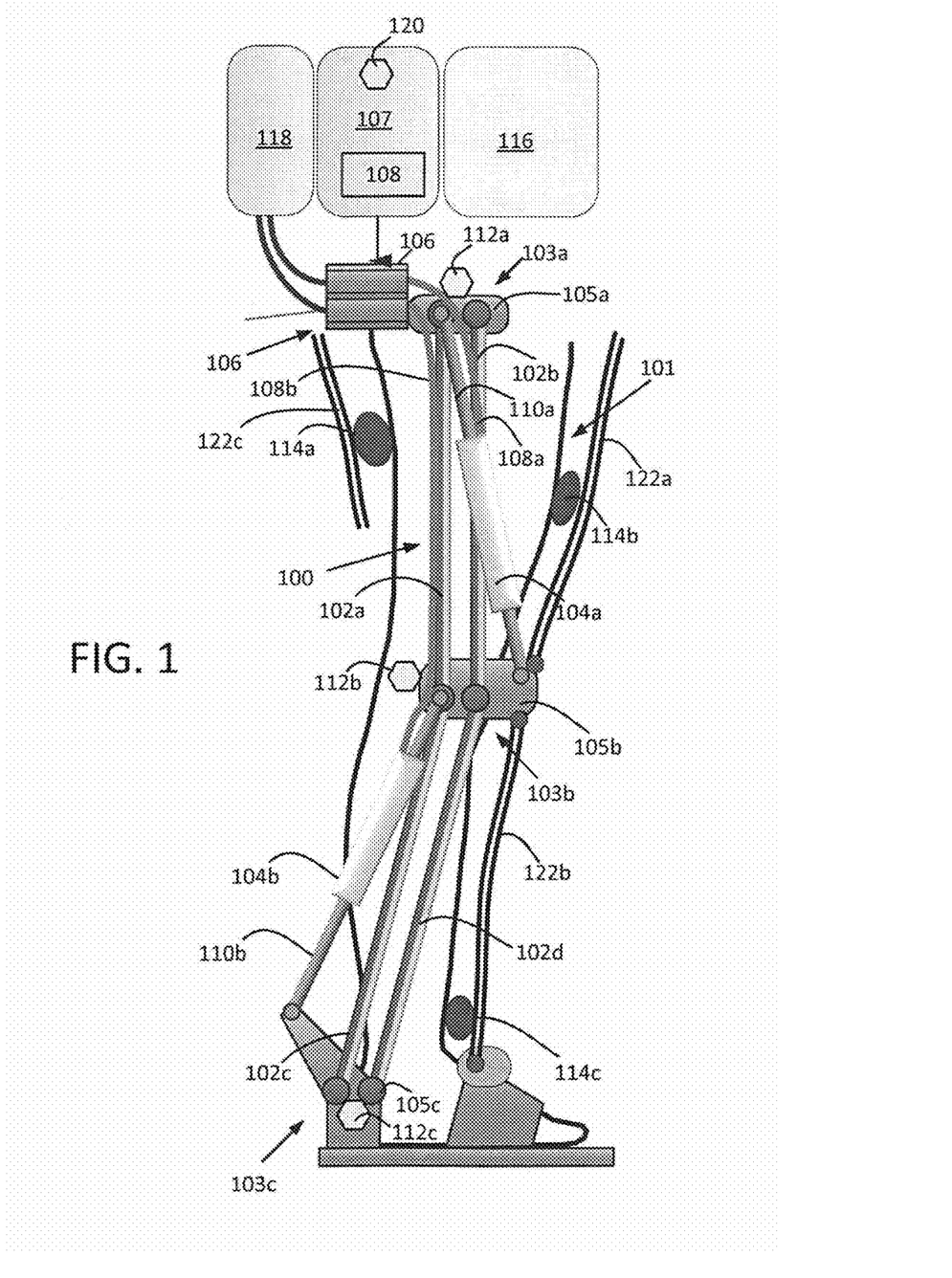
FIG. 1 is a drawing that is useful for understanding the various elements of an exoskeleton.

Referring now to FIG. 1 there is shown a portion of an exemplary exoskeleton 100 that is useful for understanding the inventive arrangements. For convenience, the portion of the exoskeleton shown in FIG. 1 is from the waist down. However, it should be understood that the invention described herein can also apply to other selected portions of an exoskeleton, such as an upper portion of an exoskeleton worn on an upper body part of user. The exoskeleton 100 is formed of a plurality of rigid structural members 102*a*, 102*b*, 102*c*, and 102*d* which are connected to each other at a plurality of joint locations 103*a*, 103*b*, 103*c* where one or more robot joints 105*a*, 105*b*, 105*c* are provided.

The joint locations are arranged to facilitate movement of the rigid structural members in a manner that at least partially corresponds to movement in accordance with the anatomy of a human user when the exoskeleton is being worn by such user. For example, when a user 101 who wears the exoskeleton 100 bends his knee, the structural members 102*a*, 102*b*, 102*c*, and 102*d* will pivot at robot joint 105*b* to facilitate such user movement. Other portions of the exoskeleton can be similarly designed to facilitate movement with the user. Consequently, the rigid structural members and the plurality of robot joints comprising an exoskeleton can be fitted to and move with at least one portion of a user 101. For example, the body portions can include all or part of an upper body portion which extends above the waist, a lower body portion which extends below the waist, and a full body portion comprising the upper and lower body.

The exoskeleton 100 also includes one or more motion actuators (e.g. motion actuators 104*a*, 104*b*). One or more of the motion actuators can be comprised of pneumatic actuators such as pneumatically operated pistons as shown. Still, the invention is not limited in this regard and other types of motion actuators may also be used. For example, one or more of the motion actuators can optionally be comprised of hydraulic actuators, and/or electric motors.

In operation, the motion actuators exert motive forces directly or indirectly upon the structural members to facilitate movement and other operations associated with the exoskeleton. For example, in the case of the pneumatic type actuators shown in FIG. 1, pressurized gas or air is communicated to an internal cylinder (not shown) associated with the actuator. The operation of pneumatic actuators is well known in the art and therefore will not be described here in detail. However, it will be appreciated that the pressurized air in the cylinder can move an internal piston (not shown) that is coupled to a rod 110*a*, 110*b*. The rod is connected to the exoskeleton structure at a suitable location, such as robot joint 105*a*, 105*c*. The flow of pressurized air or gas to the cylinder of the pneumatic actuator can be communicated by any suitable means such as pneumatic air lines 108*a*, 108*b*. One or more valves 106 can control a flow of air to the pneumatic actuators.

An outer cover for the exoskeleton can be comprised of one or more cover portions (e.g. cover portions 122*a*, 122*b*, 122*c*). The cover portions will partly or completely enclose portions of the exoskeleton and/or the person wearing such exoskeleton. The outer cover can be attached to the rigid structural members (e.g. rigid structural members 102*a*, 102*b*, 102*c*, and 102d). Alternatively, or in addition the outer cover can be attached to one or more of robot joints (e.g. robot joints 105a, 105b, 105c). The cover portions (e.g. cover portions 122a, 122b, 122c) of the exoskeleton can complement the function of the structural members (e.g. rigid structural members 102a, 102b, 102c, and 102d) to provide some of the necessary structural rigidity for the exoskeleton. In some instances, the functionality of the rigid structural members comprising the exoskeleton can be combined with the functionality of the cover portions. In such embodiments, one or more of the cover portions can serve as both a cover and as part of an integrated structural framework of the exoskeleton.

In FIG. 1, cover portions 122a, 122b are shown as extending over a front portion of an exoskeleton 100 to partially enclose a user 101. Cover portion 122c extends over a back portion of exoskeleton 100. However, it will be appreciated that the cover portions can extend over greater or lesser parts of the exoskeleton. The cover portions are rigid or semi-rigid structural members which are advantageously provided to protect the operator and/or the internal components of the exoskeleton.

A control system 107 can facilitate operator control of the exoskeleton actuators to carry out exoskeleton movements and operations. A control system 107 used with the inventive arrangements can comprise any suitable combination of hardware and software to carry out the control functions described herein. As such, the control system can comprise a computer processor programmed with a set of instructions, a programmable micro-controller or any other type of controller. The control system is arranged to communicate with one or more controlled elements for carrying out the interface control functions described herein. For example, in the exemplary exoskeleton system 100 shown in FIG. 1, the controlled elements can include motion actuators 104a, 104b.

The exoskeleton will include a plurality of sensors which communicate sensor data to the control system 107. For example, sensors 112a, 112b, 112c can be provided at one or more robot joints to provide sensor data regarding a position, a displacement and/or an acceleration of one or more structural members 102a, 102b, 102c, 102d relative to other parts of the exoskeleton. Additional sensors 114a, 114b, 114c can be provided to sense movements or forces exerted by the user 101 upon the exoskeleton 100. Output sensor data from these additional sensors 114a, 114b, 114c can be interpreted by control system 107 as control signals which can cause certain operations of the motion actuators. For example, the control system can respond to inputs from such sensors to activate certain motion actuators for effecting movement of the exoskeleton. Finally, one or more sensors 120 can optionally be provided to measure acceleration and or velocity of an exoskeleton 100 as a whole relative to an external frame of reference (e.g. relative to the earth). Connections between the various sensors and the control system are omitted in FIG. 1 to avoid obscuring the invention. However, it will be appreciated by those skilled in the art that suitable wired or wireless connections are provided to communicate sensor data from each sensor to the control system.

A suitable power source 116 is provided for powering operations of the exoskeleton. The power source can provide a source of electrical power for electronic components, such as the control system. The power source can comprise a battery, a fuel-based power generator or a tethered connection to an external power source. For exoskeletons that use pneumatic or hydraulic actuators, the exoskeleton can also include a source 118 of pressurized air or hydraulic fluid. The power source 116 and the source 118 of pressurized air can be carried on-board the exoskeleton or can be provided from a remote base unit by means of a tether arrangement.

Before describing the inventive arrangements in further detail, it is useful to more fully understand the differences between the implementation of the controlled activity mode and the explosive mode as referenced above. The "controlled activity" mode can be implemented by having the control system command the motion actuators within the exoskeleton to produce a force/torque which is just sufficient so that the weight of the exoskeleton is supported. Additional force/torque can then be provided by a user as necessary to move the exoskeleton in a particular direction.

Alternatively, the exoskeleton can provide the additional force/torque (e.g., using one or more motion actuators). In that case, the force/torque provided is such that if the exoskeleton contacts an object, the contact force between the exoskeleton and the object is substantially equal to the force that the operator is applying to the exoskeleton at that point within the exoskeleton. This can be accomplished through the use of sensors (e.g. encoders, accelerometers) to determine the exoskeleton configuration and orientation with respect to gravity. The sensors are used to determine the actuator effort which is needed to compensate for the weight of the exoskeleton. Concurrently, force and/or position sensors are used to determine the motion of the operator and the operator's contact forces against the exoskeleton. As a result, the forces on the operator are substantially equal to the forces that the operator would experience if they were not wearing an exoskeleton. Additionally, the forces exerted by the exoskeleton on surrounding objects are substantially equal to the forces that the operator would be exerting on these objects if the operator were performing the same tasks without an exoskeleton.

Exoskeleton operations in the "explosive activity" mode are very different as compared to the controlled activity mode. When operating in "explosive activity" mode, the controller exercises control over the exoskeleton actuators in a way that provides amplification of those forces exerted by the operator against the exoskeleton. Consider the case of lifting a very large object. One possible control method would incorporate sensing the contact forces between the operator and the exoskeleton at certain contact points, and then commanding the actuators to exert force/torque necessary to exert contact forces on the object/environment that are proportional to the operator's forces, but significantly larger. In such a system, the operator could use the exoskeleton to exert very large forces without the operator needing to exert large forces. Another case of "explosive activity" would be the case of sprinting. In this case, sensors could detect the motion (velocity and/or acceleration) of the operator's limbs as they run and provide the required actuator effort such that the exoskeleton not only matches the operator's movement, but also provides additional forces on the operator to provide assistance. For example, if the operator is running and one of their legs is striding forward, additional forces could be applied to the user's legs in the forward direction to assist with the operator's movement. By providing additional assistive forces, the operator could potentially be able to run faster than they would be able to run without the exoskeleton, and the assistive forces could also help reduce fatigue.

From the foregoing, it can naturally be understood that a response of an exoskeleton control system to operator inputs should be different in a scenario where the user is seeking to perform a controlled activity versus a scenario where the user is trying to engage in an explosive activity. In order to accommodate both types of operations with one exoskeleton, an exoskeleton control system would need to be able to respond differently to different operational scenarios. One way to achieve this result would be for the operator to determine in advance their next activity, and then manually select an appropriate operational mode for the exoskeleton controller that is consistent with the planned activity. For example, when a controlled activity is planned, the user could manually select a control system setting that will provide a controlled activity type exoskeleton response to user inputs. Conversely, when an explosive activity is planned, the user could manually select a control system behavior that facilitates explosive activity in response to input stimuli.

But in many scenarios, a person wearing an exoskeleton may need to repeatedly transition between controlled activities and explosive activities. Moreover, such transitions between different types of activities may occur frequently and at unpredictable intervals. Accordingly, it is not desirable for to rely upon an exoskeleton user to manually change a control system operational mode as described herein. In order to overcome these and other limitations, an exoskeleton control system can be designed to automatically transition from one control system mode (explosive activity mode) to a second control system mode (controlled activity mode) automatically. The solution involves a bi-modal or multi-modal controller that automatically switches between two or more control modes based on a measured level of operator effort and/or exertion.

According to one aspect of the invention, a level or magnitude of operator effort/exertion can be determined by neural and/or neuromuscular sensing. According to one aspect of the invention, such sensing can be performed by sensing electrical activity of the user. For example, the sensed electrical activity can pertain to the user's nervous system (e.g., by using EEG sensors) and/or the user's skeletal muscles (e.g., by using myoelectric sensors). Based on such measurements, the control system can be automatically switched between different operating modes (e.g., controlled activity mode vs. explosive activity mode). In one exemplary arrangement, myoelectric and/or EEG type sensors can be used to detect electrical activity associated with preparation for (and during) explosive activities. When a predetermined user neural condition or neuromuscular condition is detected based on the sensor inputs, the control system will change operating mode to provide control system functions which are consistent with the expected or anticipated operator effort/exertion. More than one control system mode is possible such that a control system may have a controlled activity mode, an explosive activity mode and one or more intermediate modes. Any suitable method can be used to sense neural and/or neuromuscular electrical activity as described herein. Also, it should be appreciated that a plurality of different types of electrical activity can be sensed for purposes of transitioning a control system mode. For example, both EEG activity and myoelectric activity can be sensed.

Figure 2:
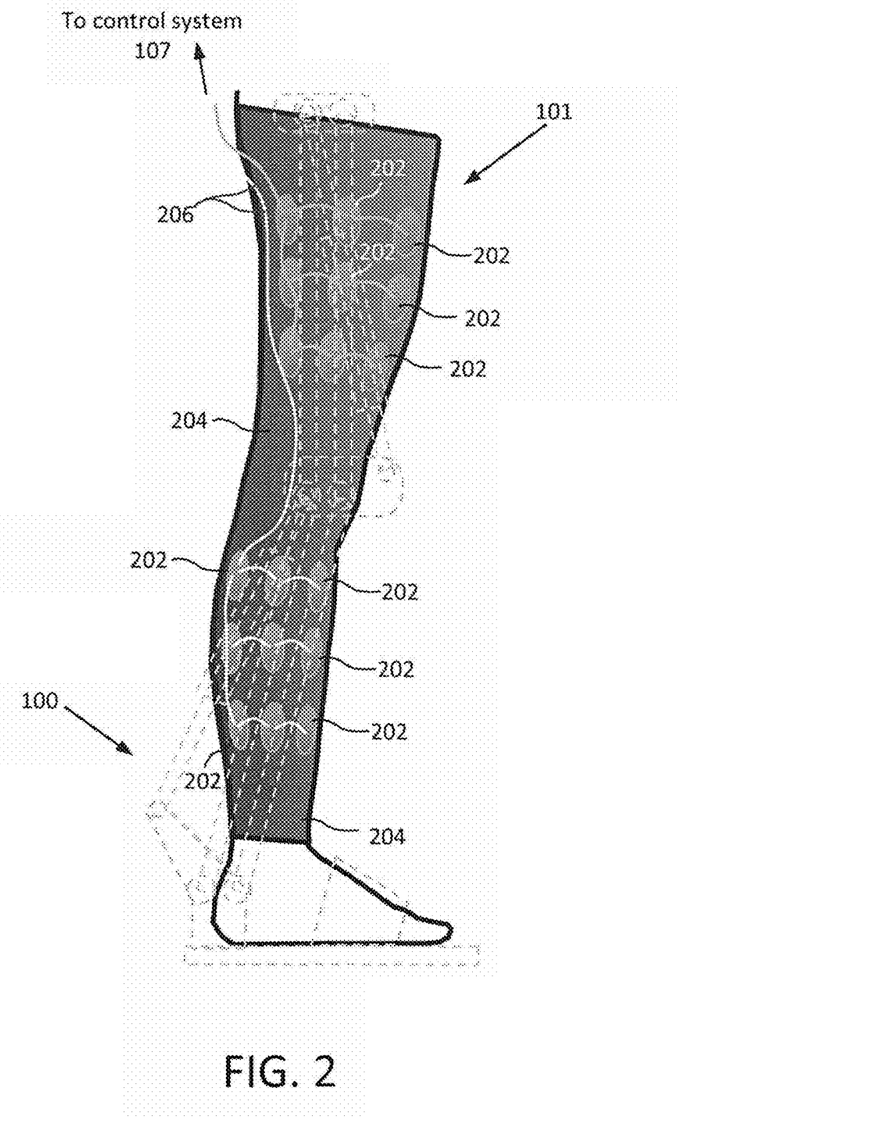
FIG. 2 is a drawing that is useful for understanding a multi-modal control system based on operator intent.

Referring now to FIG. 2, an exoskeleton system can include a plurality of sensors 202 which are disposed or arrayed on the body of a user 101 to sense electrical activity. In FIG. 2, certain portions of the exoskeleton 100 are shown in phantom to help illustrate how the electrical activity sensors 202 would be integrated into the overall system. For convenience, the sensors 202 can be disposed or attached to a close-fitting (skin-tight) elastic suit or sleeve 204 which may be worn by the user. The suit or sleeve can be formed of a fabric material which includes elastic fibers to ensure that the sensors are positioned snugly and directly on the skin of the user 101. Still, the invention is not limited in this regard and the sensors can instead be removably attached to the user's body by other means, such as adhesive. According to one aspect of the invention, the sensors can be disposed on or adjacent to muscles or groups of muscles that are known to be activated when the user engages in certain types of explosive activity. Such an arrangement is illustrated in FIG. 2. Alternatively, the electrical activity sensors can be disposed along the scalp of a user in the case of EEG type sensors. In a further alternative arrangement, both types of sensors could be used. Other electrical activity sensor locations are also possible and the invention is not intended to be limited to particular locations or the particular types of electrical activity sensors described herein.

The control system 107 is a bimodal or multi-modal controller that has the ability to control the operation of the exoskeleton responsive to user inputs in both a controlled activity mode and explosive activity mode. In some embodiments, the control system can also function in one or more intermediate modes which are designed to facilitate exoskeleton control operations for levels of user exertion that are intermediate of those associated with the controlled activity mode and the explosive activity mode. The control system 107 advantageously receives inputs from electrical activity sensors 202 to continuously sense a level of operator effort/exertion. Any suitable sensors can be used for extracting this electrical activity information. Suitable electronic or electro-optical couplings 206 are provided to communicate sensor outputs to the control system 107.

Myoelectric sensors and EEG sensors are well known in the art and therefore will not be described here in detail. However, a brief explanation may be helpful to understand how such sensors can be used in the inventive arrangements. Electromyography (EMG) involves evaluation and recording of electrical activity produced by skeletal muscles. This information can be collected using an instrument known as an electromyograph by measuring the electrical potential generated by muscle cells when are neurologically activated. Once collected, the electrical activity can be analyzed and correlated to muscle activation level, and/or to identify patterns of body movement. Once these patterns are identified and correlated with specific activities, they can be stored in a memory device associated with control system 107. Thereafter, during exoskeleton operations, when the control system receives electrical signals from the plurality of sensors, it can compare the sensed measurements with the stored patterns of electrical signals that are known to correspond to certain activities. The stored patterns of electrical signals can be stored in a memory location 108 associated with the control system 107.

Similarly, electroencephalography (EEG) is the recording of electrical activity along the scalp. EEG measures voltage fluctuations resulting from ionic current flows within the neurons of the brain. This information can be recorded by using multiple electrodes which are placed directly on the scalp. Once collected, the electrical activity can be analyzed and correlated to muscle activation level, and/or to identify patterns of body movement. Once these patterns are identified and correlated with specific activities, they can be stored in a memory device associated with control system 107. Thereafter, during exoskeleton operations, when the control system receives electrical signals from the plurality of electrical activity sensors, it can compare the sensed measurements with the stored patterns of electrical signals that are known to correspond to certain activities. The stored patterns of electrical signals can be stored in a memory location 108 associated with the control system 107.

Measured or sensed electrical activity signal patterns pertaining to user movement or pre-movement can be correlated with stored signal patterns to identify and/or predict a user motion. These same signal patterns can be evaluated to determine and/or predict a level of force to be exerted by a user and a corresponding motion velocity. In other words, with the information available from the sensors, the exoskeleton control system 107 is able to detect electrical patterns associated with preparation for explosive activities. When such signal patterns indicate that a user is about to engage in an explosive activity, a mode of control system 107 can be switched to correspond to the particular type of user action that is anticipated. If the sensor signals correspond to explosive activity, then a corresponding explosive activity mode is selected for the control system. The control system 107 can be caused to remain in such explosive activity mode for the period of time during which the sensor signals received by the control system continue to indicate the occurrence of explosive activity on the part of the user. When sensor signals corresponding to the explosive activity are no longer detected, the control system can revert to a different mode, such as the controlled activity mode, or any intermediate operation mode.

According to a further aspect, the sensed data from the electrical activity sensors can be enhanced or supplemented with data gathered by other sensors within the exoskeleton (e.g. position sensors, force sensors). For example, sensors 112a, 112b, 112c can be used for this purpose to provide sensor data regarding a position, a displacement and/or an acceleration of one or more structural members 102a, 102b, 102c, 102d relative to other parts of the exoskeleton. Sensors 114a, 114b and 114c can also be used for this purpose. The additional inputs provided by these sensors can be used to more accurately predict the desired control system mode of operation. For each type of intended activity that is sensed, the control system will select the appropriate control system mode of operation. Although the concept is illustrated in FIGS. 1 and 2 with respect to the lower body, it should be understood that the concept as described herein is in fact applicable to the entire exoskeleton.

The sensed electrical patterns that are used to select a control system mode can also be used for other purposes. For example, it can be difficult to determine the correct user-desired movement and force of an exoskeleton accurately without delay/lag. In a conventional exoskeleton, the operator motion/force is measured (e.g. using sensors 114a, 114b, 114c), then translated into a desired motion/force by the exoskeleton control system and actuators. This necessarily results in the movements of the exoskeleton lagging behind those of the operator. Some exoskeletons partially address this problem by taking advantage of certain types of repetitive motions. For example, in the case of walking, the exoskeleton control system may assume a steady gait. But this type of solution to the problem only works for cyclic or repetitive motion.

A better solution to the problem involves sensing operator intent (i.e. pre-motion) to determine correct movements in a manner which substantially reduces or eliminates the time delay/lag problem noted above. Operator pre-motion can be detected via sensing of user electrical activity in a manner similar to that described above with respect to control system mode selection. For example, electrical activity sensors as described above can be used for this purpose. The control system will contain stored data concerning electrical activity patterns which uniquely correspond to pre-motion electrical signals before and during certain types of motion. During exoskeleton operations the control system will analyze signals received from the plurality of sensors disposed on an operator. A pattern of electrical signals from such sensors is analyzed to determine if it correlates to a particular pre-motion signal pattern stored in a memory location in the control system. When such a pre-motion signal pattern is identified, the exoskeleton control system 107 can begin generating signals to one or more motion actuators. The signals to the motion actuators are selected to generate actual exoskeleton movement that corresponds to the identified pre-motion signal set. The control system can continue to monitor the inputs from sensors 202 as well as other sensors as described herein to ensure that the actual exoskeleton motion is consistent with user intentions.

Figure 3:
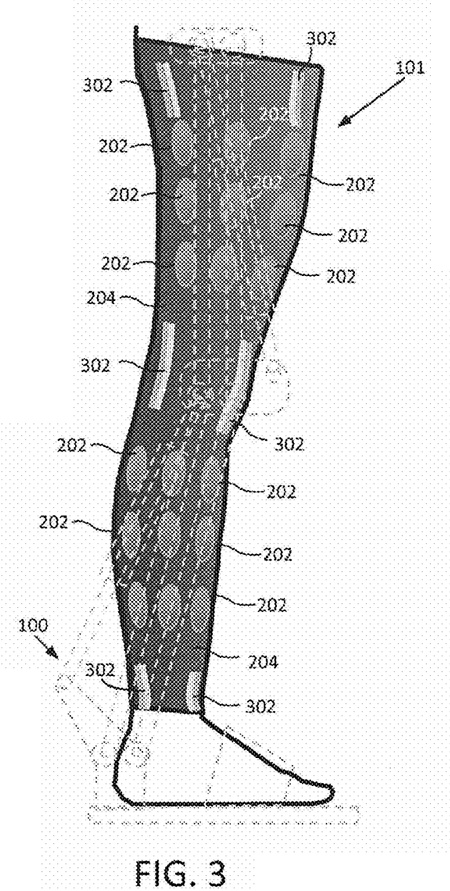
FIG. 3 is a drawing that is useful for understanding a multi-modal control system which includes a first type of displacement sensing.

Additional sensors can be provided that measure actual operator displacement. Such an arrangement is illustrated in FIG. 3 which shows how additional sensors 302 can be embedded in the inner suit or sleeve 204. For example, a plurality of strain-based sensors can be provided to detect variations in operator position. The data from these physical motion sensors will provide more accurate indications of user motion as compared to data obtained exclusively from sensors 202. The combined data obtained from the electrical activity sensors (e.g. sensors 202) and sensors 302 will facilitate optimal control system performance because they will provide the most accurate and complete information to the control system 107 for purposes of determining the required exoskeleton motion. Initial motion of an exoskeleton can be triggered by pre-motion sensing (for low delay), and actual desired position of the exoskeleton can be based on sensed operator motion (for better position accuracy). More particularly, user electrical activity sensing (e.g., using sensors 202) is used for at least motion initiation. Thereafter, position sensing with sensors 302 can be used to ensure that motion/position control signals generated by the control system 107 accurately correspond to actual movements of the user.

Figure 4:
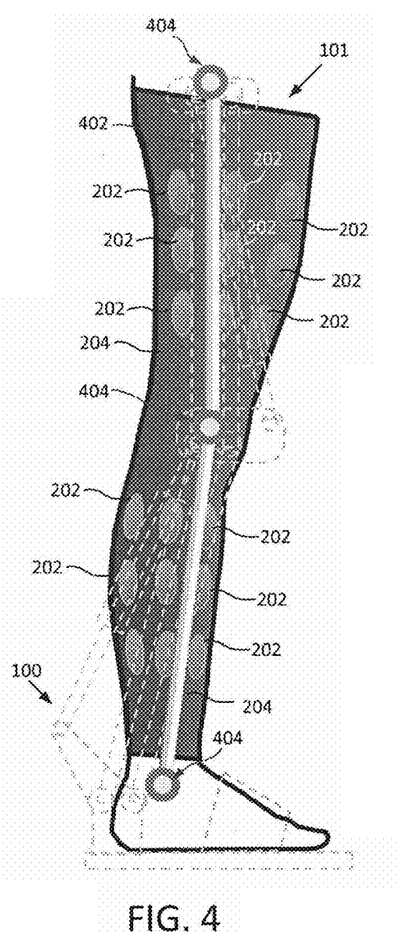
FIG. 4 is a drawing that is useful for understanding a multi-modal control system which includes a second type of displacement sensing.

Referring now to FIG. 4, there is shown an alternative embodiment of the inventive arrangements which includes a light-weight inner exoskeleton 402 which is disposed inside the exoskeleton 100. The light-weight inner exoskeleton is separate from the remaining structural elements comprising the exoskeleton 100. Accordingly, small changes in user position which may be insufficient to cause movement of the structural elements 102a, 102b, 102c, 102d movement will produce a detectable movement of elements comprising the inner exoskeleton 402. Motion sensing encoders (e.g. optical encoders) 404 placed at certain user joints of the inner exoskeleton 402 can be used to detect actual physical motion of the operator, even under conditions where no motion occurs or is detected at that otherwise comprise the exoskeleton. Sensors 112a, 112b, 112c are designed to sense motion of the exoskeleton structural members (e.g., structural members 102a, 102b, 102c, 102d). In contrast, motion sensing encoders 404 detect user motions within the exoskeleton, which can be different from motions of the exoskeleton itself. The motion sensing encoders 404 in this embodiment are used in place of (or in addition to) the strain sensors 302 to supplement information provided by sensors 202.

Those skilled in the art will appreciate that the arrangements shown and described with respect to FIGS. 1-4 can comprise exoskeleton control systems which include electrical activity sensors (e.g., myoelectric sensors, EEG sensors) in combination with displacement and/or strain sensors that measure operator movement. Additional force/torque sensors 114a, 114b, 114c can be provided as well to sense forces exerted by the operator upon the exoskeleton. The interaction forces between the operator and the exoskeleton are sensed and the sensed information can thereafter be used by the control system (e.g. control system 107) to aid in controlling the motion of the exoskeleton. Sensed operator forces applied against the exoskeleton are used to command the exoskeleton to exert forces in the desired direction. As with other embodiments described herein, initial motion of the exoskeleton can be triggered by pre-motion sensing (e.g. using user electrical activity sensors) for low delay. Actual desired force is more precisely determined and exerted based on sensed operator force/effort. Accordingly, sensors 114a, 114b, and 114c can be used alone or in combination with the other types of sensors described herein to work in conjunction with the electrical activity sensors. The electrical activity sensors reduce lag by sensing pre-motion (i.e., a user intention to move in advance of actual user movement), whereas the force sensors measuring user forces exerted upon the exoskeleton provide a basis for more accurate sensing with respect to the precise amount of force that the user intends the exoskeleton to exert upon the external environment.

Figure 5:
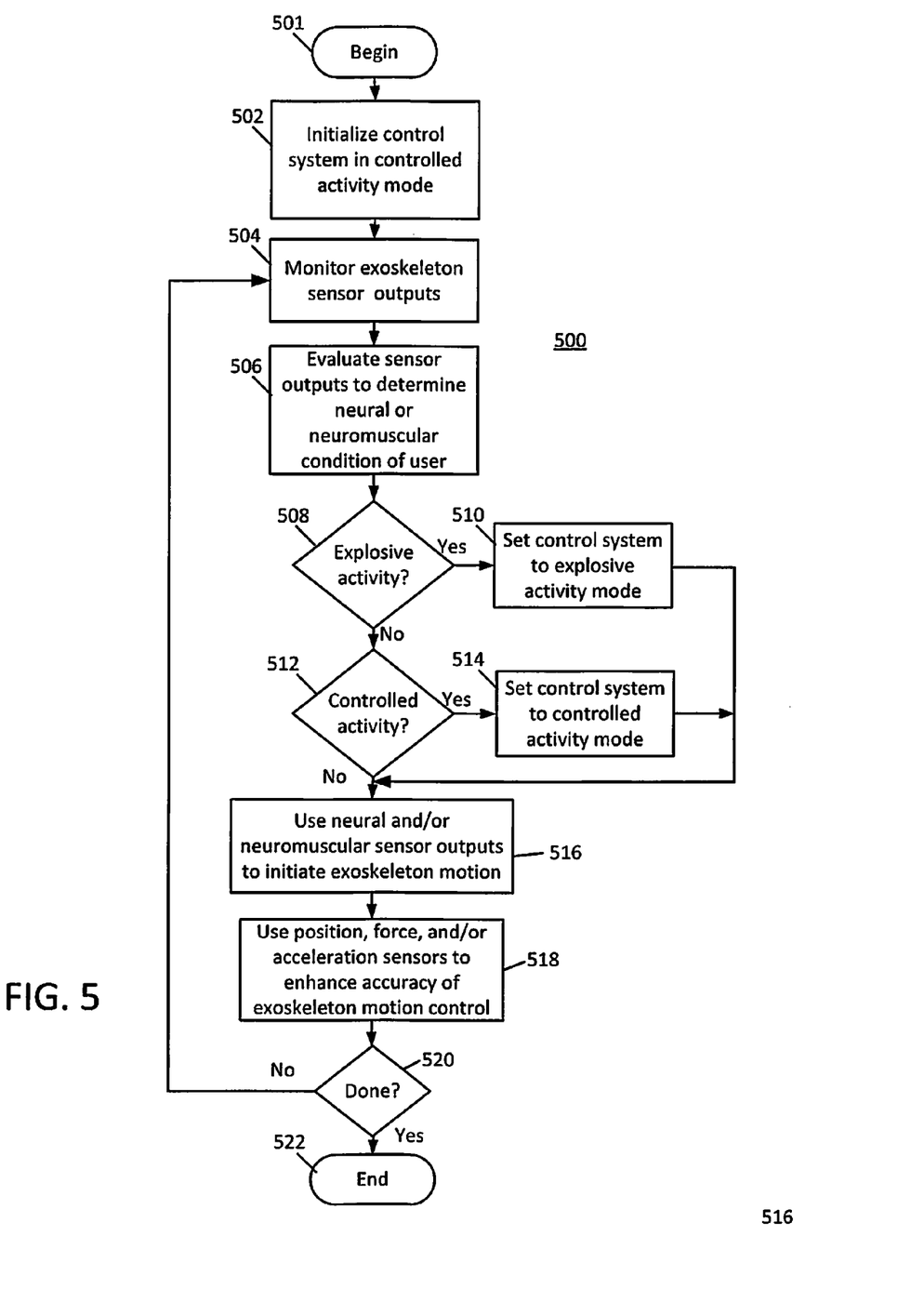
FIG. 5 is a flow chart that is useful for understanding an exoskeleton control system.

Turning now to FIG. 5, there is provided a flowchart 500 that is useful for understanding a method for controlling an exoskeleton using the electrical activity sensors described herein. The method begins at 501 and continues to 502 at which an exoskeleton control system is initially set in a controlled activity mode. The control system will remain in this mode unless evaluation of sensor outputs indicates that a change is required. In step 504 the exoskeleton control system monitors exoskeleton sensor outputs. For example, an exoskeleton control system 107 can monitor a plurality of electrical activity sensors 202 which are arranged to sense electrical potentials generated by a user. In step 506, the electrical activity sensor outputs are evaluated to determine whether they indicate an occurrence of a particular neural or neuromuscular condition of the user. For example, this evaluation can involve a comparison of the sensor outputs to stored patterns of electrical activity. In one embodiment, the purpose of this comparison would be to determine whether a particular sensed pattern of electrical activity is closely correlated to a pre-determined pattern of electrical activity stored in a memory location of the exoskeleton control system.

In step 508, a determination is made as to whether a measured or sensed pattern of electrical activity is indicative of a predetermined neural or neuromuscular condition which corresponds to explosive activity. For example, a determination could be made as to whether the measured or sensed pattern of electrical activity is correlated to a pre-determined stored pattern that indicates explosive activity. If so (508: Yes), the control system is automatically set to an explosive activity mode at 510. In the explosive activity mode, the control system behavior is optimized for explosive activity. If a determination is made that the sensed pattern of electrical activity does not correspond to a neural and/or neuromuscular condition associated with explosive activity (508: No) then the process continues on to step 512. In step 512, a determination is made as to whether the sensed pattern corresponds to controlled activity. For example, the sensed neural or neuromuscular electrical activity is analyzed to determine if it corresponds to a predetermined neural and/or neuromuscular condition of controlled activity. If so, (512: Yes) then the control system is set in step 514 to the controlled activity mode. If the control system is already in the controlled activity mode, then it will remain in that mode.

Thereafter at 516 the process can continue by using the outputs of the electrical activity sensors to reduce delay time when initiating exoskeleton motions. In step 518, the force, direction, and/or acceleration of the initial motion is fine-tuned using position, force and/or acceleration sensors so as to more accurately determine the user's intended motion for the exoskeleton. At 520 a determination is made as to whether the process should be terminated. If so, then the process ends at 518; otherwise the process returns to step 504 and continues.

It will be appreciated that only two separate control system modes are provided for in the flowchart 500. Specifically, the process seeks to identify explosive activity and controlled activity and then chooses a control system mode accordingly. However, the invention is not limited in this regard and additional control system operating modes intermediate of explosive activity and controlled activity mode are also possible.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

We claim:

1. An exoskeleton, comprising:
an exoskeleton comprised of a plurality of structural members, one or more robotic joints at which the plurality of structural members are movably attached, and a plurality of actuators connected to the plurality of structural members which are capable of providing a motive force for moving the plurality of structural members in relation to the robotic joints, the plurality of structural members and robotic joints arranged to facilitate movement of the exoskeleton in conformance with at least a portion of a human anatomy when the exoskeleton is worn by a user;
a controller which generates actuator control signals that control the plurality of actuators in response to a plurality of input signals to produce a movement of the exoskeleton;
at least one electrical activity sensor arranged to sense electrical signals associated with a body of the user of the exoskeleton;
wherein the controller (1) identifies a pre-stored sensor pattern from a plurality of pre-stored sensor patterns that has a given correlation with a measured sensor pattern specifying an occurrence of a particular neural or neuromuscular condition of the user and (2) automatically sets the controller's operating mode to a controller operating mode of a plurality of different operating modes which is associated with the pre-stored sensor pattern which was previously identified; and
wherein the plurality of different operating modes comprise a first operating mode in which the controller controls the plurality of actuators in a way that closely matches a force exerted by the user and a second operating mode in which the controller controls the plurality of actuators in a way that provides amplification of the force exerted by the user.

2. The exoskeleton according to claim 1, wherein the first operating mode comprises a controlled activity operating mode and the second operating mode comprises an explosive activity operating mode.

3. The exoskeleton according to claim 1, wherein the controller initiates a movement of the exoskeleton based on outputs received from the at least one electrical activity sensor.

4. The exoskeleton according to claim 3, further comprising at least one of a position sensor, a force sensor, and an acceleration sensor coupled to the controller and arranged to sense a user motion.

5. The exoskeleton according to claim 4, wherein the controller after initializing the movement of the exoskeleton, utilizes an output signal from at least one of the position sensor, the force sensor and the acceleration sensor to determine an exoskeleton motion based on said user motion with greater accuracy as compared to an accuracy obtained by using only the at least one electrical activity sensor.

6. The exoskeleton according to claim 1, wherein the controller controls the movement of the exoskeleton based on inputs received from the at least one electrical activity sensor and from at least one additional sensor for detecting a user motion, the at least one additional sensor selected from the group consisting of a position sensor, a force sensor and an acceleration sensor.

7. The exoskeleton according to claim 1, wherein the at least one electrical activity sensor comprises a sensor selected from the group consisting of a myoelectric sensor and an electroencephalography sensor.

8. The exoskeleton according to claim 7, wherein the output is comprised of a plurality of signals respectively provided by the plurality of electrical activity sensors.

9. A method for operating a robotic exoskeleton worn by a human operator, comprising:
   using a control system to monitor an output of at least one electrical activity sensor-disposed on the human operator when wearing the robotic exoskeleton to directly sense electrical signals associated with a body of the human operator;
   determining if an output of the at least one electrical activity sensor indicates an occurrence of a predetermined neural or neuromuscular condition of the human operator;
   identifying a pre-stored sensor pattern from a plurality of pre-stored sensor patterns that has a given correlation with the output that indicates the occurrence of the predetermined neural or neuromuscular condition of the human operator; and
   automatically setting the control system's mode to an operating mode of a plurality of different operating modes which is associated with the pre-stored sensor pattern which was previously identified;
   wherein the plurality of different operating modes comprise a first operating mode in which the control system controls a plurality of actuators in a way that closely matches a force exerted by the human operator and a second operating mode in which the controller system controls the plurality of actuators in a way the provides amplification of the force exerted by the human operator.

10. The method according to claim 9, further comprising generating with the control system actuator control signals that control one or more actuators of the exoskeleton responsive to a control motion of the human operator.

11. The method according to claim 9, wherein the first operating mode comprises an controlled activity operating mode and the second operating mode comprises an explosive activity operating mode.

12. The method according to 9, further comprising monitoring with the control system an output of at least one of a position sensor, a force sensor, and an acceleration sensor to determine a user motion.

13. The method according to claim 12, further comprising using the output from the electrical activity sensor to initiate an exoskeleton motion, and then using at least one of the position sensor, the force sensor and the acceleration sensor to more precisely determine the parameters of the motion which has been initiated.

14. The method according to claim 9, wherein the output is comprised of a plurality of signals respectively provided by the plurality of electrical activity sensors.

* * * * *